United States Patent
Webb et al.

(10) Patent No.: US 6,358,477 B1
(45) Date of Patent: Mar. 19, 2002

(54) URINE SPECIMEN COLLECTION DEVICE

(75) Inventors: Belinda Webb, 6429 Chaprice La., Montgomery, AL (US) 36117; Pamela Rhodes, Montgomery, AL (US)

(73) Assignee: Belinda Webb, Montgomery, AL (US)

( * ) Notice: Subject to any disclaimer, the term of this patent is extended or adjusted under 35 U.S.C. 154(b) by 0 days.

(21) Appl. No.: 09/414,095

(22) Filed: Oct. 7, 1999

(51) Int. Cl.⁷ .................................................. B01L 3/00
(52) U.S. Cl. ........................ 422/102; 422/99; 600/573; 600/580; 4/144.1; 4/144.2
(58) Field of Search ................... 422/99, 102; 600/573, 600/574, 580; 4/144.1, 144.2, 144.3

(56) References Cited

U.S. PATENT DOCUMENTS

| | | | | |
|---|---|---|---|---|
| 3,466,145 A | | 9/1969 | Van Duyne | 422/103 |
| 3,571,817 A | * | 3/1971 | Gosnell | 4/144.1 |
| 3,625,654 A | | 12/1971 | Van Duyne | 422/102 |
| 4,040,791 A | | 8/1977 | Kuntz | 422/102 |
| 4,137,573 A | | 2/1979 | Kroeger | 4/144.1 |
| 4,203,169 A | * | 5/1980 | Dale | 73/863.52 |
| 4,276,889 A | | 7/1981 | Kuntz et al. | 600/574 |
| 4,309,782 A | | 1/1982 | Paulin | 4/661 |
| 4,331,162 A | * | 5/1982 | Kuntz et al. | 600/574 |
| 4,554,687 A | * | 11/1985 | Carter et al. | 4/144.2 |
| 4,569,090 A | * | 2/1986 | Muller | 4/144.2 |
| 5,095,556 A | * | 3/1992 | Franey | 4/460 |
| 5,146,637 A | * | 9/1992 | Bressler et al. | 4/445 |
| 5,457,823 A | * | 10/1995 | Mojena | 4/144.2 |
| 5,537,693 A | * | 7/1996 | Dossola et al. | 4/245.4 |
| 5,655,229 A | * | 8/1997 | Horn | 4/144.3 |
| 5,913,832 A | * | 6/1999 | Sagalovich et al. | 600/573 |
| 5,920,916 A | * | 7/1999 | Norton | 4/144.3 |
| 6,115,855 A | * | 9/2000 | Lorenzo | 4/484 |
| 6,151,972 A | * | 11/2000 | Venter et al. | 73/863.41 |

\* cited by examiner

*Primary Examiner*—Maureen M. Wallenhorst
(74) *Attorney, Agent, or Firm*—Baker, Donelson, Bearman & Caldwell

(57) ABSTRACT

A collection device (10, 50) for urine samples in which a support (14, 56) is received on a seat of a commode. The support includes a funnel (16, 52) that depends from a first edge of the support about a perimeter thereof and tapering inwardly defines an open distal end (18, 52) opposed to the first edge. A collection cup (24, 60) is removably attached to the distal end of the funnel. The collection cup, being disposed inwardly of a commode with the support received on a seat thereof, receives a urine specimen from a patient occupying the commode and the collection cup, being detached from the funnel, carries the sample for analysis while the remainder of the collection device is disposed of.

16 Claims, 2 Drawing Sheets

URINE SPECIMEN COLLECTION DEVICE

TECHNICAL FIELD

The present invention relates to devices for collecting urine samples. More particularly, the present invention relates to urine specimen collection devices that are conveniently used with conventional commodes while being sufficiently low-cost for single-use disposal.

BACKGROUND OF THE INVENTION

Fluid samples often are received from patients for analysis to evaluate the medical status of the patients. Urine is one such fluid that is routinely sampled for analysis. Urine specimens are delivered by the patients into collection cups which are closed and transported for analysis. Delivery of such specimens, however, generally is an awkward and onerous activity, particularly for young children, women, and seriously ill patients.

Devices have been provided in the past which attempt to facilitate the collection of urine specimens. These provide collection devices that have specimen receptacles and attaching members for mounting the devices to rims of commodes. The attaching members support the receptacles that are positioned within the bowl cavity of the commodes. Channels direct the fluid specimen into the receptacles. Other such devices include special containments in order to obtain selected portions of the specimen, while disposing of the remainder.

While such devices have been useful for obtaining specimens, there are drawbacks to the use of such. The attaching member can become released inadvertently, which may lead to loss of the specimen. The receptacle in readily manufactured, blow molded collection devices is not removable. This device requires a subsequent transfer of the specimen to a second collection container for transport to analysis. Other devices are structurally complicated for selective sampling. Such is not practical for routine sampling.

Accordingly, there is a need in the art for an improved collection device for obtaining urine samples. It is to such that the present invention is directed.

SUMMARY OF THE INVENTION

The present invention meets the needs in the art by providing a urine specimen collection device for urine samples comprising an at least U-shaped planar support plate for being received on a seat of a commode. A funnel formed of a substantially water impermeable flexible sheet material attaches to a first surface of the support plate and depends from a first edge from the support plate about a perimeter thereof and tapers inwardly to define a distal end opposed to the first edge. The sheet material defines a plurality of spaced-apart perforations about the distal end. A collection cup open to a fluid receiving surface of the funnel removably attaches to the distal end of the funnel. The collection cup, being disposed inwardly of the commode with the support plate received thereon, receives a urine specimen from an occupant of the commode. The collection cup being detached from the funnel by severing the funnel at the perforations, carries the urine specimen for analysis while the support plate and funnel of the collection device is disposed of.

In another aspect, the present invention provides a disposable collection device for obtaining urine samples, in which a funnel is defined by a flexible substantially water impermeable sheet material. The funnel attaches at a first edge to a seat of a commode and the sheet material tapers away therefrom and inwardly to define an open distal end opposed to the first edge. The sheet material defines a plurality of spaced-apart perforations about the distal end. An elongate securing member disposed at the first edge is selectively moved to an elongated position for disposing the funnel on the seat of the commode and to a retracted position for engaging the seat. A collection cup open to a fluid receiving surface of the funnel is removably supported in the open distal end of the funnel. The collection cup, being disposed inwardly of commode with the funnel received on the seat thereof upon moving the securing member between the retracted and elongated positions, receives a urine specimen flowing on at least a portion of the fluid receiving surface of the funnel from an occupant of the commode. The collection cup, being detached from the funnel by severing the funnel at the perforations, carries the urine specimen for analysis while the remainder of the collection device is disposed of.

In yet another aspect, the present invention provides a disposable collection device for obtaining urine samples, comprising a funnel defined by a flexible sheet material attached at a first edge to a seat of a commode and tapering away therefrom and inwardly to define an open distal end opposed to the first edge. An elongate elastic band disposed at the first edge is selectively moveable to an elongated position for disposing the funnel on the seat of the commode and to a retracted position for engaging the seat. A collection cup is removably supported in the open distal end of the funnel. The collection cup, being disposed inwardly of commode with the funnel received on the seat thereof, receives a urine specimen flowing on at least a portion of an inner surface of the funnel from an occupant of the commode, and the collection cup, being detached from the funnel, carries the sample for analysis while the remainder of the collection device is disposed of.

Objects, advantages and features of the present invention will become apparent from a reading of the following detailed description of the invention and claims in view of the appended drawings.

DETAILED DESCRIPTION OF THE PREFERRED EMBODIMENTS

Figure 1:
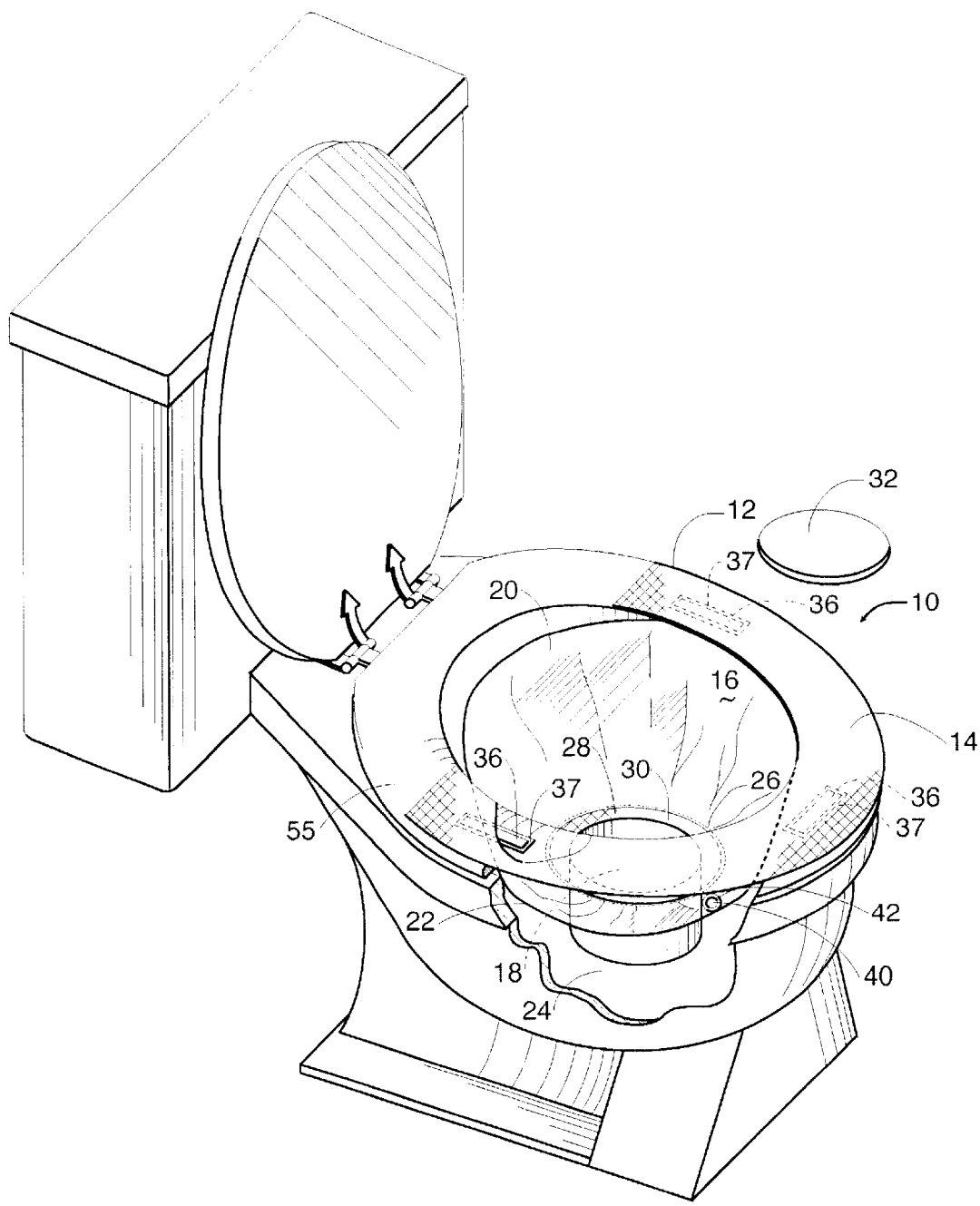
FIG. 1 is a perspective view of a collection device for urine samples according to the present invention.

Referring now in more detail to the drawings in which like parts have like identifiers, FIG. 1 illustrates in perspective view a collection device generally 10 for obtaining urine samples according to the present invention. The collection device 10 includes a support 12 that is adapted for being received on a seat of a commode. In the embodiment illustrated in FIG. 1, the support 12 comprises a plate 14. The plate 14 is preferably formed of a sturdy, yet lightweight material such as paperboard, fibreboard, plastic, or latex materials, which is readily sanitized or sterilized for insertion into a sterile wrapper for packaging prior to use. The support plate 14 defines in plan view a U-shape planar sheet that is readily received on a seat of a commode. In an alternate embodiment, the support plate 14 defines a continuous sheet having an oval or circular shape in plan view. In another alternate embodiment, the support 14 comprises a pair of opposing members for being received on the upper surface of a seat for a commode.

A funnel 16 attaches at a first edge to the support 12 and tapers narrowingly away from the support to an open distal end 18 opposing the first edge. In the illustrated embodiment, the funnel 16 attaches around a perimeter of the support plate 14, whereto define an opening 20 inwardly of the plate. The funnel 16 extends away from the plate 14 and tapers inwardly to define a distal end 22 opposed to the first edge and at defining the opening 18. The funnel 16 preferably comprises a flexible sheet material that attaches at a first edge to the support plate 14. The funnel 16 preferably attaches with an adhesive to the support plate 14. The sheet material is preferably a thin plastic film. The sheet material can also be a substantially water impermeable paper or the like.

A collection cup 24 removably attaches to the distal end 22 and extends through the opening 18. The cup 24 is paper, plastic, or other conventional material suitable for sample collection and retention. A plurality of perforations 26 extend around the opening in the distal end spaced-apart from a rim 28 of the cup. In the illustrated embodiment, an annular ring 30 attaches to the distal end 22 as a support for the collection cup 24. The ring 30 attaches with an adhesive. The cup 24 detachably receives a cap 32 (shown exploded away), whereby the cup is selectively open and closed. As discussed below, the cap 32 is removed when disposing the cup 24 within a commode for collecting a urine sample and replaced to transport the sample for analysis.

In the illustrated embodiment, the distal end of the funnel 16 attaches with an adhesive to an inner surface of the collection cup 24. In an alternate embodiment, the collection cup 24 is provided separately from the funnel 16 and the support 12. The cup 24 is received through the opening 18 of the funnel 16 prior to disposing the cup within a commode for collecting a urine sample.

In a preferred embodiment, patches 36 (illustrated in FIG. 1) of an adhesive material attach to a lower surface of the support plate 14 for adhereingly engaging the support plate to a seat of a commode, as discussed below. The patches 36 are preferably a double-sided tape cut to length and attached to the support plate 14. The exterior face of the patches 36 are covered with a removable film or sheet 37.

In the illustrated embodiment, a portion of the funnel 16 defines a first opening 40, which is used for draining an overflow portion of the urine sample into the commode after collection and before recovery of the collection cup 24. An annular ring 42 provides a rigid support around the opening 40 which facilitates the draining of the overflow.

Figure 2:
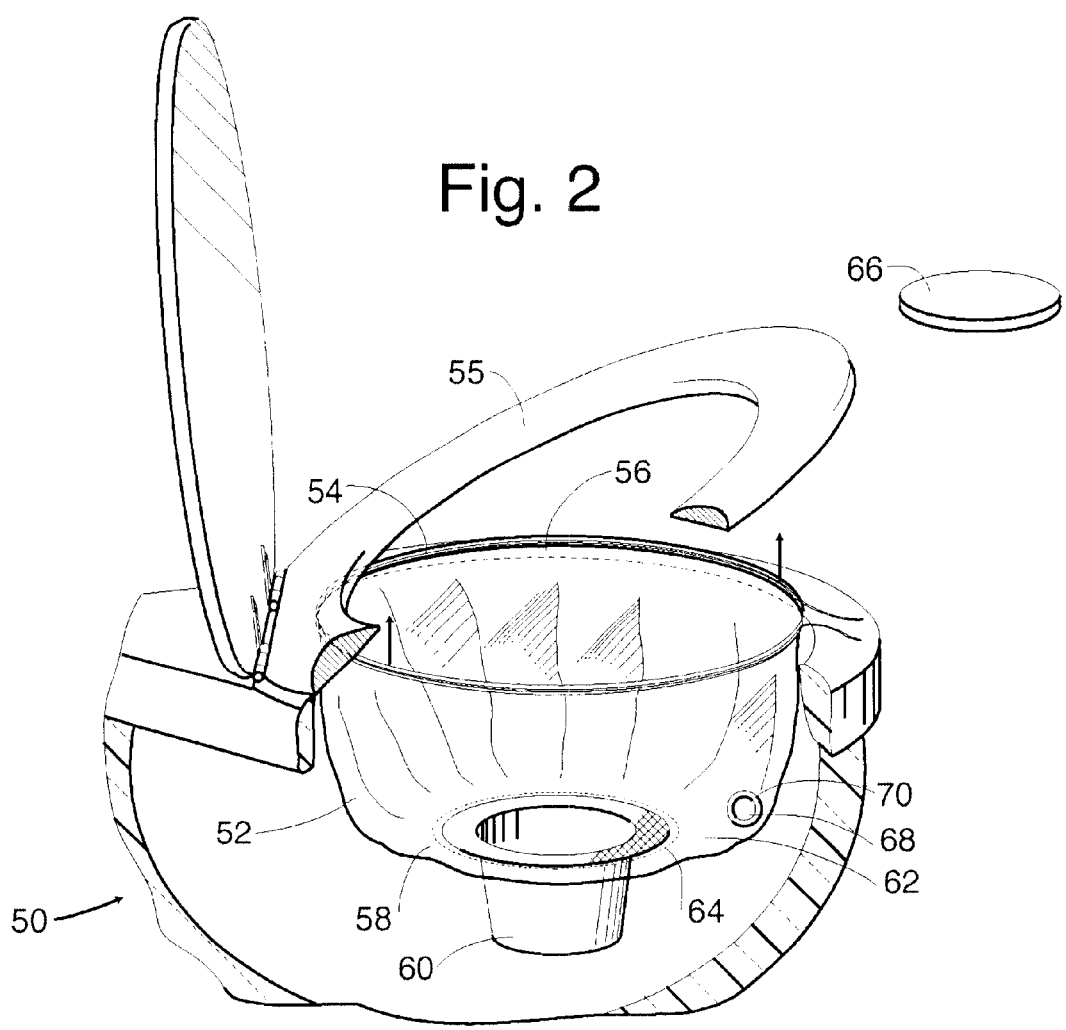
FIG. 2 is a perspective view of a second embodiment of the collection device for urine samples according to the present invention.
Figure 3:
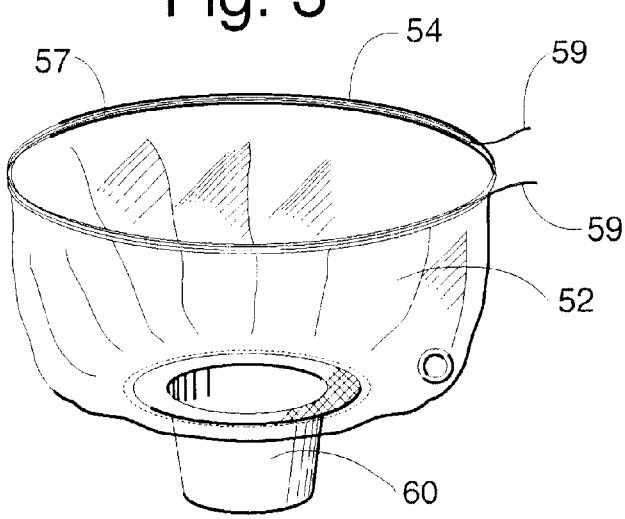
FIG. 3 is a perspective view of an alternate embodiment of the collection device illustrated in FIG. 2.

FIG. 2 illustrates in perspective view a second embodiment 50 of the collection device for urine samples according to the present invention. The collection device 50 includes a funnel 52 that is defined by a flexible plastic sheet material. The funnel 52 includes a first edge 54 adapted for attaching at the first edge to a seat 55 of a commode. In the illustrated embodiment, the first edge 54 includes an elongate elastic band 56 disposed within an overlapping portion of the sheet material. This defines an elastic portion at the first edge 54 which is selectively elongatable to a first position and biased to a relaxed position. The edge 54 thereby defines an opening of a large diameter with the elastic portion stretchingly extended to the first position. In the relaxed position, the open edge 54 defines a smaller diameter opening for the funnel. The elastic band 56 stretches to the elongated position for disposing the funnel on the seat 55 of the commode. The elastic band 56 relaxes to a intermediate retracted position for engaging the funnel 52 to the seat 55. In an alternate embodiment (not illustrated) the first edge portion of the funnel defines a reinforced rolled edge and the portion is generally thicker than the depending portion of the funnel, whereby the edge portion defines the support adapted to be received on the seat. In an alternate embodiment illustrated in FIG. 3, the edge 54 defines a channel formed by overlapping a side portion and bonding together. The channel receives an elongate string 57, and opposing distal ends 59 extend outwardly through a gap. The distal ends 59 are pulled in order to grippingly engage the alternate embodiment to the seat 55 of a commode.

The funnel 52 extends from the first edge 54 tapering inwardly to define an open distal end 58 opposed to the first edge 54. The open distal end 58 removably receives a cup 60 for collecting a urine sample.

In a first embodiment, the distal end portion 58 of the funnel 52 attaches with an adhesive to an inner surface of the cup 60. A plurality of spaced-apart perforations 62 extend around the distal end portion of the funnel, spaced-apart from a rim of the cup 60. The perforations 62 allow the collection cup 60 to be readily detached from the funnel 52 by tearing along the perforations.

In an alternate embodiment, the cup 60 is provided separately from the funnel 52. In this embodiment (also illustrated in FIG. 2), an annular support ring 64 disposed about the open end provides a support for receiving the collection cup 60. An alternate embodiment includes both the perforations 62 and the support ring 64.

The cup 60 detachably receives a cap 66 whereby the cup is selectively open and closed. As discussed below, the cap 66 is removed when disposing the cup 60 within a commode for collecting a urine sample and replaced to transport the collected sample for analysis.

In the illustrated embodiment, a portion of the funnel 52 defines a first opening 68, which is used for draining an overflow portion of the urine sample into the commode after collection and before recovery of the collection cup 60. An annular ring 70 provides a rigid support around the opening 68 which facilitates the draining of the overflow.

The collection device 10 is used for collecting urine samples. With reference to FIG. 1, a first embodiment of the device 10 is prepared for use by removing the cap 32 from the cup 24. The adhesive patches 36 are exposed by removing the respective sheets 37. The support plate 14 is then positioned on the seat of a commode (partially illustrated in phantom). The adhesive patches 36 secure the device 10 to the seat of the commode. The funnel 16 extends downwardly into the bowl of the commode, with the cup 24 extending downwardly therefrom. The patient occupies the seat, and provides a urine specimen. The specimen flows along the funnel 16 into the collection cup 24. The collection cup 24 is thereafter separated from the device 10 and closed with the cap 32 for transport of the specimen for analysis. In one embodiment, the collection cup 24 is separated by tearing the perforations 26. A portion of the sheet material of the funnel 16 remains attached to the collection cup 24, and defines a seal between the cup and the cap 22. It is noted that the apparatus of the present invention is suitable for disposing between a rim of a commode and a seat thereof, whereby the rim and the seat clamp the collection device therebetween with the funnel and collection cup depending into the bowl of the commode. Although not illustrated, the cap can be conventionally threaded for engaging a thread on the cup. Other conventional securing mechanisms can be usefully employed to secure the cap to the cup.

In the embodiment in which the cup 24 is provided separately from the support 14 and the funnel 16, the cap 32 is removed. The cup 24 is then slidingly received through the opening 18, with the rim bearing against the support ring 30. After collection of the specimen, the cup is removed and closed with the cap 22.

In the embodiment having the drain opening 40, overflow of the specimen is discharged through the opening into the commode prior to removing the collection cup 24.

With reference FIG. 2, the collection device 50 is attached to the seat 55 of the commode by elongating the first edge 54 to the larger diameter. The seat 55 receives the large open end of the funnel 52. The elastic band 58 retracts upon release to an intermediate position for securing the device 50 to the seat 55 with the funnel 52 extending inwardly into the bowl of the commode and the cup 60 extending downwardly therefrom. In the embodiment illustrated in FIG. 3, the seat 55 receives the open end at the edge 54. The distal ends 59 of the string 57 are pulled and tied to secure the collection device to the seat 55.

The patient occupies the seat, and provides a urine specimen. The specimen flows along the funnel 52 into the collection cup 60. The collection cup 60 is thereafter separated from the device 50 and closed with the cap 66 for transport of the specimen for analysis. In one embodiment, the collection cup 60 is separated by tearing the perforations. A portion of the sheet material of the funnel 52 remains attached to the collection cup 60, and defines a seal between the cup and the cap 66.

In the embodiment in which the cup 60 is provided separately from the funnel 52, the cap 66 is removed from the cup. The cup 60 is then slidingly received through the opening at the distal end 58, with the rim of the cup bearing against the support ring 64. After collection of the specimen, the cup 60 is removed and closed with the cap 66.

In the embodiment having the drain opening 68, overflow of the specimen is discharged through the opening into the commode prior to removing the collection cup 24. The ring 70 provides support for the opening 68 in the funnel 52, which facilitates draining the overflow from the device 50.

The present invention accordingly provides a disposable specimen collection device readily manufactured with a collection cup that being disposed inwardly of commode with the funnel received on the seat thereof, receives a urine specimen flowing on at least a portion of an inner surface of the funnel from a patient, and being detached from the funnel, carries the sample for analysis while the remainder of the collection device is disposed of. The specimen collection device can be provided in a sanitary protective wrapping which is opened prior to use. The patient thereby sits on a clean, sanitary surface of the plate 14 or the edge 54. The collection cup is readily removed after the deposit of the specimen, and the remaining portions of the collection device are placed in a sanitary trash receptacle for disposal.

The principles, preferred embodiments, and modes of operation of the present invention have been described in the foregoing specification. The invention is not to be construed as limited to the particular forms disclosed because these are regarded as illustrative rather than restrictive. Moreover, variations and changes may be made by those skilled in the art without departure from the spirit of the invention as described by the following claims.

What is claimed is:

1. A collection device for obtaining urine samples, comprising:
   an at least U-shaped planar support plate for being received on a seat of a commode;
   a funnel formed of a substantially water impermeable flexible sheet material attached to a first surface of the support plate and depending from a first edge from the support plate about a perimeter thereof and tapering inwardly to define a distal end opposed to the first edge, the sheet material defining a plurality of spaced-apart perforations about the distal end; and
   a collection cup open to a fluid receiving surface of the funnel removably attached to the distal end of the funnel,
      whereby the collection cup, being disposed inwardly of the commode with the support plate received thereon, receives a urine specimen from an occupant of the commode and being detached from the funnel by severing the funnel at the perforations, carries the urine specimen for analysis while the support plate and funnel of the collection device is disposed of.

2. The collection device as recited in claim 1, wherein the support plate is made of a sheet material.

3. The collection device as recited in claim 1, wherein the support plate is defined by a plate formed of a paperboard material.

4. The collection device as recited in claim 1, further comprising an annular support ring received in the distal end for supporting the collection cup therein.

5. The collection device as recited in claim 1, further comprising a cap detachably received on the collection cup to selectively open and close the collection cup, whereby the cap is removed when disposing the collection cup within the commode for collecting the urine specimen.

6. The collection device as recited in claim 1, wherein the collection cup is provided separately from the funnel, which collection cup is engaged to the distal end thereof prior to disposing the collection cup within the commode for collecting the urine specimen.

7. The collection device as recited in claim 1, wherein a portion of the funnel defines a first opening spaced-apart from the distal end and intermediate the distal end and the first edge for draining an overflow portion of the urine specimen into the commode.

8. The collection device as recited in claim 7, further comprising a support ring disposed around the first opening.

9. A disposable collection device for obtaining urine samples, comprising:
   a funnel defined by a flexible substantially water impermeable sheet material attached at a first edge to a seat of a commode and the sheet material tapering away therefrom and inwardly to define an open distal end opposed to the first edge, the sheet material defining a plurality of spaced-apart perforations about the distal end;
   an elongate securing member disposed at the first edge and being selectively moved to an elongated position for disposing the funnel on the seat of the commode and to a retracted position for engaging the seat; and
   a collection cup open to a fluid receiving surface of the funnel removably supported in the open distal end of the funnel,
      whereby the collection cup, being disposed inwardly of the commode with the funnel received on the seat thereof upon moving the securing member between the retracted and elongated positions, receives a urine specimen flowing on at least a portion of the fluid receiving surface of the funnel from an occupant of the commode, and being detached from the funnel by severing the funnel at the perforations, carries the urine specimen for analysis while the remainder of the collection device is disposed of.

10. The collection device as recited in claim 9, wherein the securing member is an elongate elastic band.

11. The collection device as recited in claim 9, wherein the securing member is an elongate string having distal ends extending outwardly of the funnel.

12. The collection device as recited in claim 9, further comprising an annular support ring received in the distal end for supporting the collection cup therein.

13. The collection device as recited in claim 9, further comprising a cap detachably received on the collection cup to selectively open and close the collection cup, whereby the cap is removed when disposing the collection cup within the commode for collecting the urine specimen.

14. The collection device as recited in claim 9, wherein the collection cup is provided separately from the funnel, which collection cup is engaged to the distal end thereof prior to disposing the collection cup within the commode for collecting the urine specimen.

15. The collection device as recited in claim 9, wherein a portion of the funnel defines a first opening spaced-apart from the distal end and intermediate the distal end and the first edge for draining an overflow portion of the urine specimen into the commode.

16. The collection device as recited in claim 15, further comprising a support ring disposed around the first opening.

* * * * *